(12) United States Patent
Funa et al.

(10) Patent No.: US 10,487,313 B2
(45) Date of Patent: Nov. 26, 2019

(54) EFFICIENT INDUCTION OF DEFINITIVE ENDODERM FROM PLURIPOTENT STEM CELLS

(71) Applicants: Novo Nordisk A/S, Bagsvaerd (DK); Takara Bio Europe AB, Goteberg (SE)

(72) Inventors: Nina Funa, Lund (SE); Katja Hess, Lund (SE); Jenny Ekberg, Malmoe (SE); Henrik Semb, Bjaerred (SE)

(73) Assignees: Novo Nordisk A/S, Bagsvaerd (DK); Takara Bio Europe AB, Bagsvaerd (DK)

( * ) Notice: Subject to any disclaimer, the term of this patent is extended or adjusted under 35 U.S.C. 154(b) by 0 days.

(21) Appl. No.: 15/705,705

(22) Filed: Sep. 15, 2017

(65) Prior Publication Data

US 2018/0002668 A1   Jan. 4, 2018

Related U.S. Application Data

(63) Continuation of application No. 14/127,296, filed as application No. PCT/EP2012/062013 on Jun. 21, 2012, now abandoned.

(60) Provisional application No. 61/501,351, filed on Jun. 27, 2011.

(30) Foreign Application Priority Data

Jun. 21, 2011 (EP) .................................. 11170713

(51) Int. Cl.
C12N 5/0735 (2010.01)
C12N 5/071 (2010.01)
C12N 5/074 (2010.01)

(52) U.S. Cl.
CPC ......... *C12N 5/0678* (2013.01); *C12N 5/0606* (2013.01); *C12N 5/0676* (2013.01); *C12N 5/0696* (2013.01); *C12N 2501/115* (2013.01); *C12N 2501/16* (2013.01); *C12N 2501/40* (2013.01); *C12N 2506/02* (2013.01)

(58) Field of Classification Search
CPC .................................................. C12N 5/0606
See application file for complete search history.

(56) References Cited

U.S. PATENT DOCUMENTS

| | | | |
|---|---|---|---|
| 5,942,435 A | 8/1999 | Wheeler | |
| 6,417,185 B1 | 7/2002 | Goff et al. | |
| 8,932,853 B2 | 1/2015 | Hosoya et al. | |
| 9,062,292 B2 | 6/2015 | Coleman | |
| 9,133,439 B2 | 9/2015 | Davis et al. | |
| 2006/0148081 A1 | 7/2006 | Kelly et al. | |
| 2007/0254359 A1 | 11/2007 | Rezania et al. | |
| 2008/0066197 A1 | 3/2008 | Ying et al. | |
| 2009/0298178 A1 | 12/2009 | D'Amour | |
| 2009/0325293 A1 | 12/2009 | Davis et al. | |
| 2009/0325294 A1 | 12/2009 | Nelson | |
| 2010/0028307 A1 | 2/2010 | O'Neil | |
| 2010/0062527 A1 | 3/2010 | Pera et al. | |
| 2010/0099186 A1 | 4/2010 | Perry et al. | |
| 2010/0151568 A1 | 6/2010 | D'Amour et al. | |

FOREIGN PATENT DOCUMENTS

| | | |
|---|---|---|
| CN | 101684454 A | 3/2010 |
| WO | 02092756 A2 | 11/2002 |
| WO | 03050249 A2 | 6/2003 |
| WO | 2005/063971 A2 | 7/2005 |
| WO | 2005/116073 A2 | 12/2005 |
| WO | 2007/103282 A2 | 9/2007 |
| WO | 07/127927 A2 | 11/2007 |
| WO | 07143193 A1 | 12/2007 |
| WO | 2008/094597 A2 | 8/2008 |
| WO | 2009/013254 A1 | 1/2009 |
| WO | 09012428 A2 | 1/2009 |
| WO | 2009018453 A1 | 2/2009 |
| WO | 2009/027654 A1 | 3/2009 |
| WO | 2009048675 A1 | 4/2009 |
| WO | 09132068 A2 | 10/2009 |
| WO | 2009132063 A1 | 10/2009 |
| WO | 09137844 A2 | 11/2009 |
| WO | 2009/154606 A1 | 12/2009 |
| WO | 10002785 A1 | 1/2010 |
| WO | 2010002846 A1 | 1/2010 |
| WO | 2010051213 A1 | 5/2010 |
| WO | 2010051223 A1 | 5/2010 |
| WO | 2010057039 A2 | 5/2010 |
| WO | 2010091241 A2 | 8/2010 |
| WO | 2010124142 A2 | 10/2010 |
| WO | 2010/138750 A2 | 12/2010 |
| WO | 11011300 A2 | 1/2011 |
| WO | 2011011302 A2 | 1/2011 |
| WO | 2011079017 A2 | 6/2011 |
| WO | 2011079018 A2 | 6/2011 |
| WO | 11109279 A2 | 9/2011 |

(Continued)

OTHER PUBLICATIONS

Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Jean et al. (2013, Develop. Growth Differ., vol. 55, pp. 41-51) (Year: 2013).*
Buta et al. (2013, Stem Cell Res., vol. 11, pp. 552-562) (Year: 2013).*
D'Amour et al. (2006, Nature Biotechnology, vol. 24(11), pp. 1392-1401) (Year: 2006).*

(Continued)

*Primary Examiner* — Thaian N Ton
*Assistant Examiner* — David A. Montanari
(74) *Attorney, Agent, or Firm* — Leon Y. Lum

(57) ABSTRACT

The present invention relates to a method to differentiate pluripotent stem cells to a primitive streak cell population, in a stepwise manner for further maturation to definitive endoderm.

12 Claims, 11 Drawing Sheets

(56) References Cited

FOREIGN PATENT DOCUMENTS

| WO | 11140441 | A2 | 11/2011 |
|---|---|---|---|
| WO | 2011143299 | A2 | 11/2011 |
| WO | 11160066 | A1 | 12/2011 |
| WO | 12021698 | A2 | 2/2012 |
| WO | 12030538 | A2 | 3/2012 |
| WO | 12030539 | A2 | 3/2012 |
| WO | 12070014 | A2 | 5/2012 |
| WO | 2012/078153 | A1 | 6/2012 |
| WO | 12081029 | A1 | 6/2012 |
| WO | 2012175633 | A1 | 12/2012 |

OTHER PUBLICATIONS

Bone et al., (e-Published May 24, 2011, J. Cell Sci., vol. 124, pp. 1992-2000) (Year: 2011).*
Cohen et al. (2004, Nature Review, Drug Discovery, vol. 3, pp. 479-487) (Year: 2004).*
Synnergren et al. (2010, Stem Cells and Develop., vol. 19(7), pp. 961-978) (Year: 2010).*
NIH Guidelines 2016, 11 page pdf. (Year: 2016).*
Kroon et al., Nature Biotechnology, 'Pancreatic endoderm derived from human embryonic stem cells generates glucose-responsive insulin-secreting cells in vivo', 2008, vol. 26, No. 4, 443-452.
Sumi Tomoyuki et al., Development, Defining early lineage specification of human embryonic stem cells by the orchestrated balance of canonical Wnt/?-catenin, Activin/Nodal and BMP signaling, 2008, vol. 135, 2969-2979.
Ying et al, Nature, The ground state of embryonic stem cell self-renewal, 2008, vol. 453, pp. 519-523.
Ameri, J et al. (2010) "FGF2 specifies hESC-derived definitive endoderm into foregut/midgut cell lineages in a concentration-dependent manner." Stem Cells vol. 28(1): 45-56.
Hanna, J et al. (2010) "Human embryonic stem cells with biological and epigenetic characteristics similar to those of mouse ESCs." Proct Natl Acad Sci USA vol. 107(20): 9222-9227.
Jiang, J et al. (2007) "Generation of insulin-producing islet-like clusters from human embryonic stem cells." Stem Cells vol. 25(8): 1940-1953.
Mazumdar, J et al. (2010) "O2 regulates stem cells through Wnt/beta-catenin signaling" Nat Cell Biol vol. 12(10): 1007-1013.
Sato, N et al. (2004) "Maintenance of pluripotency in human and mouse embryonic stem cells through activation of WNT signaling by a pharmacological GSK-3-specific inhibitor." Nat Med 10(1): 55-63.

Wagner, R.T. et al. (2010) "Canonical Wnt/beta-Catenin regulation of liver receptor homolog-1 (Lrh-1) Mediates Pluripotency Gene Expression" Stem Cells 1794-1804.
Yang, J. et al (2010) "Stat3 activation is limiting for reprogramming to ground state pluripotency" Cell Stem Cell vol. 7 (3): 319-328.
Hay, DC et al. (2008) "Highly efficient differentiation of hESCs to functional hepatic endoderm requires ActivinA and Wnt3a signaling" PNAS vol. 105(34): 12301-6.
Yang, Bi et al. (2009) "Wnt Antagonist SFRP3 Inhibits the Differentiation of Mouse Hepatic Progenitor Cells" J. Cell. Biochem. vol. 108: 295-303.
Agarwal, S et al. (2008) "Efficient Differentiation of Functional Hepatocytes from Human Embryonic Stem Cells" Stem Cells vol. 26: 1117-1127.
D'Amour KA et al.,Production of pancreatic hormone-expressing endocrine cells from human embryonic stem cells, Nature Biotechnology , 2006, vol. 24, No. 11, pp. 1392-1401.
Munoz, M et al. "Conventional Pluripotency Markers are Unspecific for Bovine Embryonic-Derived Cell-Lines." Theriogenology. 2008. vol. 69 pp. 1159-1164.
D.B.B.P. Paris et al. "Equine Embryos and Embryonic Stem Cells: Defining Reliable Markers of Pluripotency." Theriogenology 2010 vol. 74 pp. 516-524.
Synnergren, J. et al. "Transcriptional Profiling of Human Embryonic Stem Cells Differentiating to Definitive and Primitive Endoderm and Further Toward the Hepatic Lineage." Stem Cells and Development 2010 vol. 19(7) pp. 961-978.
Cohen, P. et al. "GSK3 Inhibitors: Development and Therapeutic Potential" Nature Review, Drug Discovery. 2004 vol. 3 pp. 479-487.
Bone, H et al. "A Novel Chemically Directed Route for the Generation of Definitive Endoderm from Human Embryonic Stem Cells Based on Inhibition of GSK-3." Journal of Cell Science. 2011 vol. 124 pp. 1992-2000.
T.A.L. Brevini et al. "Embryonic Stem Cells in Domestic Animals. No Shortcuts to Pig Embryonic Stem Cells." Theriogenology 2010 vol. 74 pp. 544-550.
Chung et al, Human embryonic stem cells lines generated without embryonic destruction, Cell Stem Cell 2, 2008, pp. 113-117.
Geens et al., Human embryonic stem cell lines derived from single blastomeres of two 4-cell stage emryos, Human Reproduction, vol. 24 (11), 2009, pp. 2709-2717.
Klimanskaya et al., Human embryonic stem cell lines derived from single blastomeres, Nature, vol. 444(23) Letters, 2006.

* cited by examiner

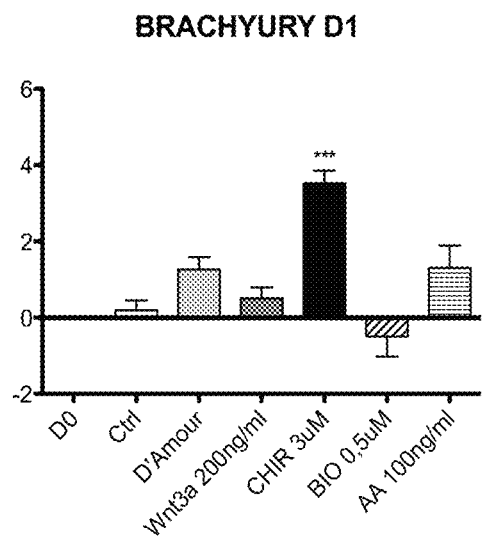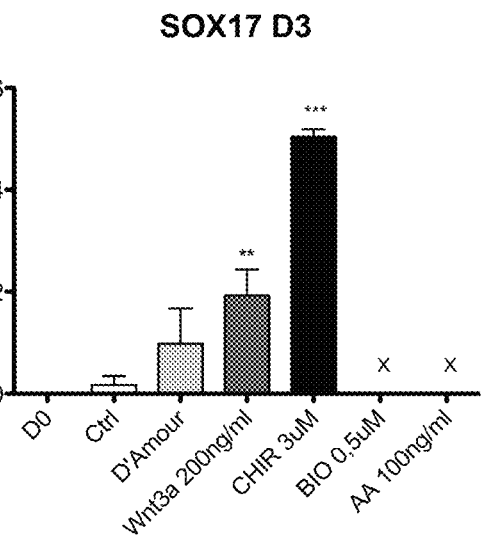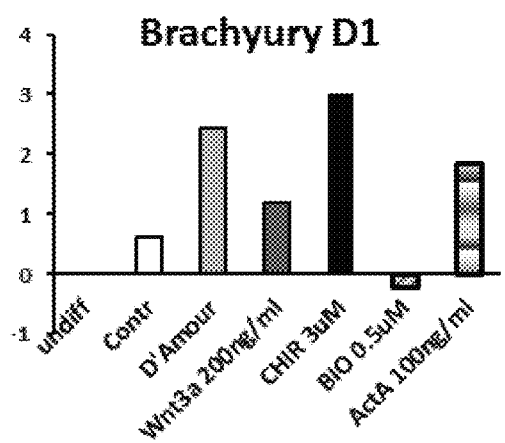
Fig. 4

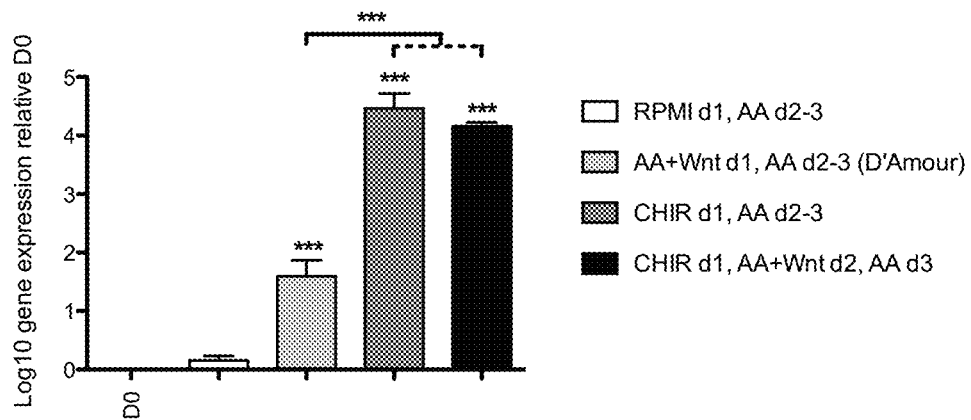
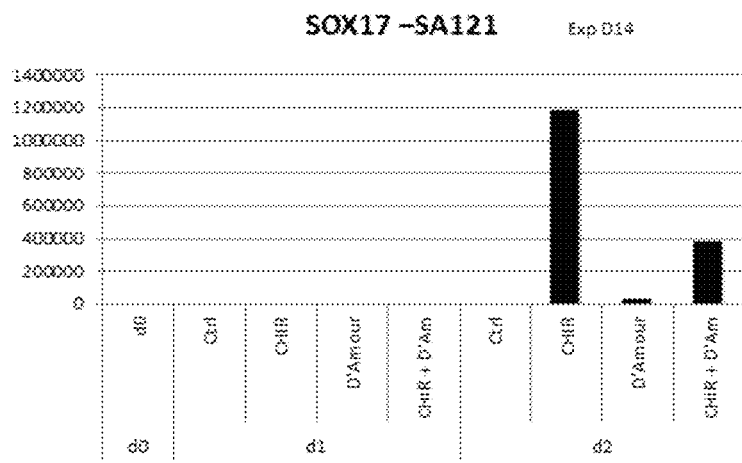
Fig. 6A,B

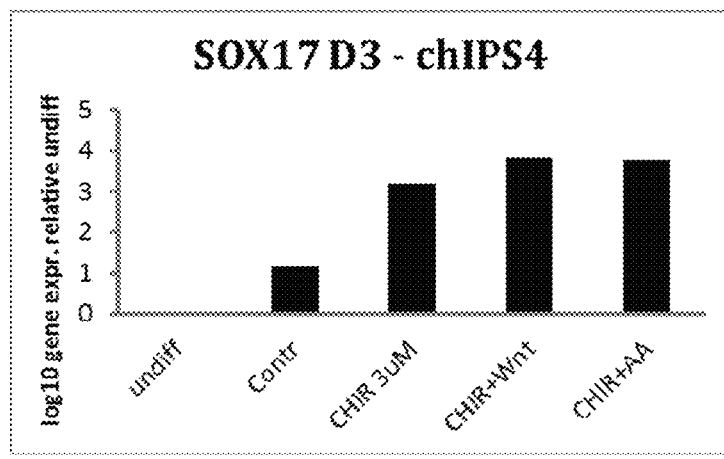
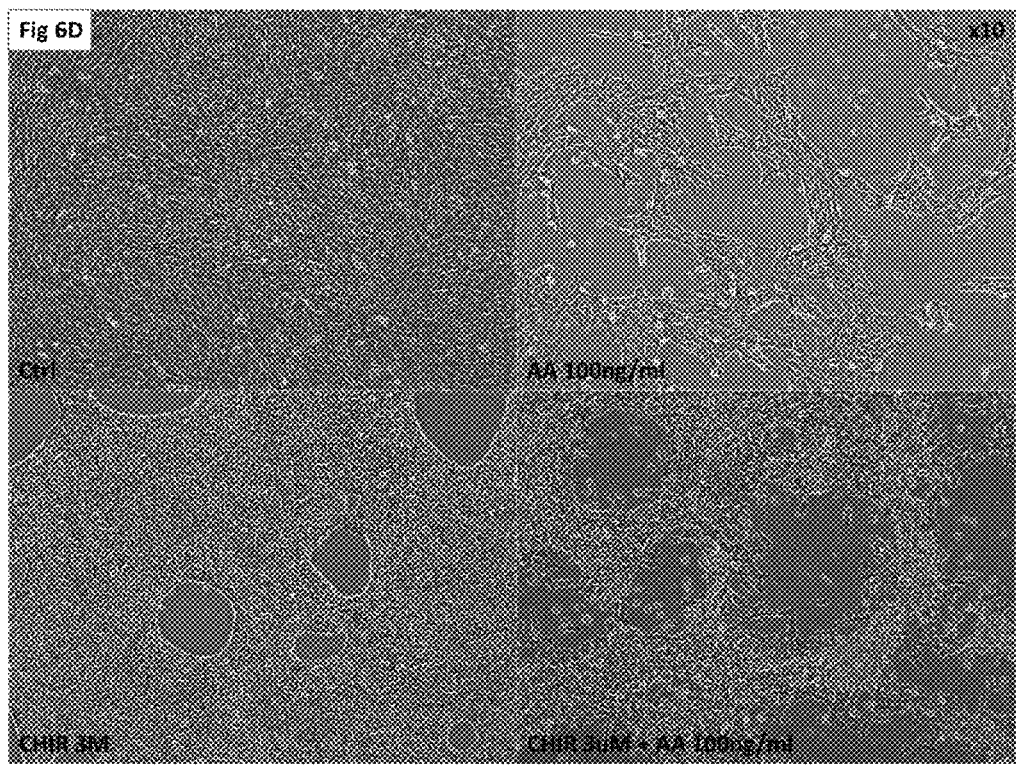
Fig. 6C,D

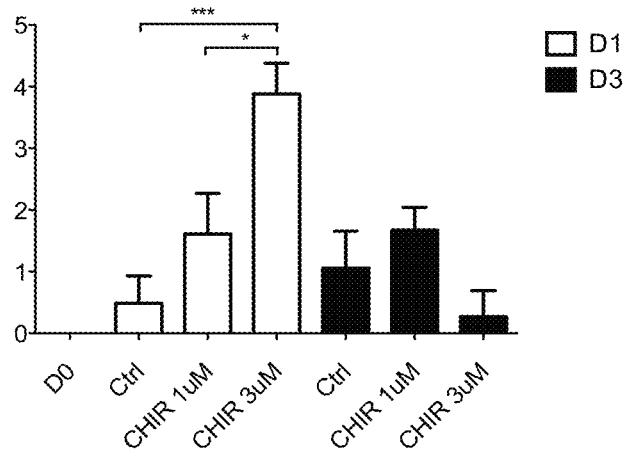
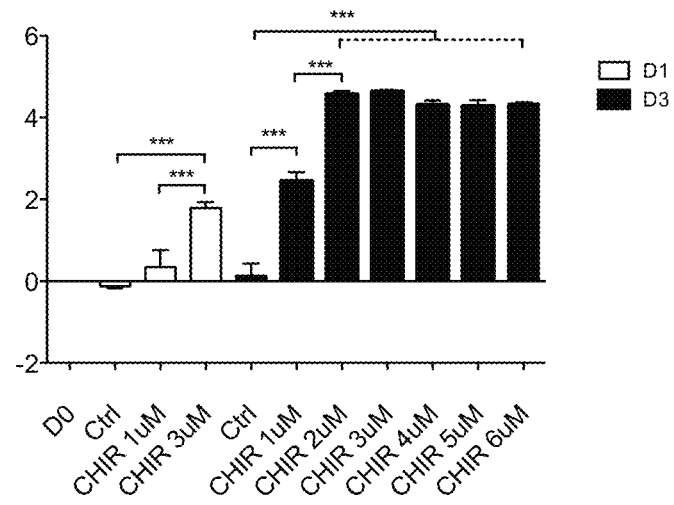
Fig. 7A,B

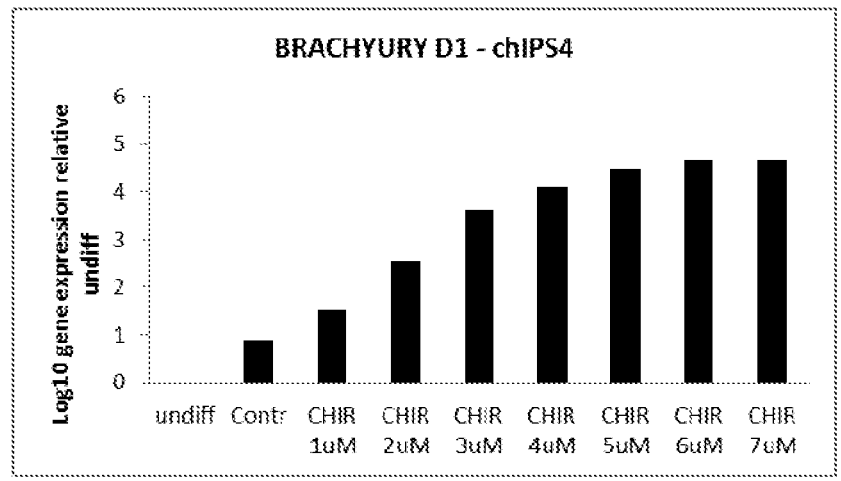
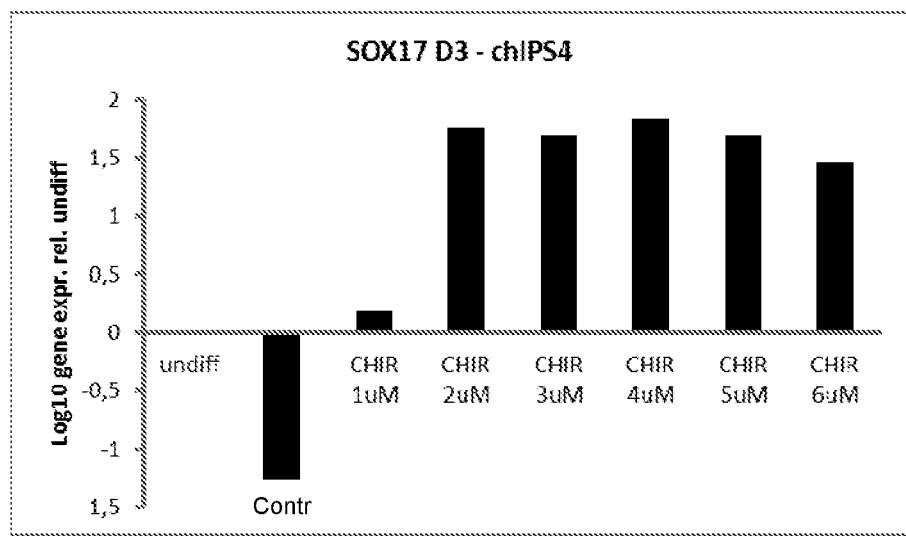
Fig. 7C,D

EFFICIENT INDUCTION OF DEFINITIVE ENDODERM FROM PLURIPOTENT STEM CELLS

CROSS-REFERENCE TO RELATED APPLICATIONS

This application is a continuation of U.S. application Ser. No. 14/127,296, filed Apr. 7, 2014,which is a 35 U.S.C. § 371 National Stage application of International Application PCT/EP2012/062013, filed Jun. 21, 2012, which claims priority to European Patent Application 11170713.9, filed Jun. 21, 2011; the parent application claims priority under 35 U.S.C. § 119 to U.S. Provisional Application 61/501,351; filed Jun. 27, 2011. The contents of all applications are incorporated herein by reference.

FIELD OF THE INVENTION

The present invention relates to a method to differentiate pluripotent stem cells to a primitive streak cell population, in a stepwise manner for further maturation to definitive endoderm.

BACKGROUND OF THE INVENTION

Transplantation of islets of Langerhans holds great promise to improve treatment of Type 1 diabetes mellitus, but the scarcity of available donor islets is one obstacle that need to be addressed. Pluripotent stem cells can in principle generate unlimited numbers of beta cells for transplantation but reliable protocols for generating fully functional beta cells are not yet developed. The foregut derivatives; pancreas, lung, thyroid, liver, esophagus, and stomach originate from definitive endoderm (DE), one of the three germ layers that forms during gastrulation. Induction of DE is the first critical step towards formation of differentiated cell types from endodermally derived tissues such as insulin producing beta cells of the pancreas. Formation of DE cells from pluripotent embryonic stem (ES) cells has been reported for both mouse and human in, e.g., WO2005/116073, WO2005/063971, and US 2006/0148081. The generation of pancreatic endoderm (PE) cells from DE cells is necessary for the generation of insulin-producing beta cells for the treatment of diabetes.

It is known that DE formation in the embryo passes through the intermediate step of primitive streak (PS) formation (a mesendodermal intermediate) which has the potential to form either mesoderm or DE. At the cellular level, all developmental processes are ultimately controlled by the cooperative actions of different signal transduction pathways. Among them, Wnt signaling is indispensable for orchestrating the complex cell behaviors that occur throughout development. Wnt signaling controls cell proliferation, stem cell maintenance and cell fate decisions, as well as organized cell movements and the establishment of tissue polarity. It is also frequently deregulated in human cancers and has been implicated in degenerative diseases. As a potential target for therapeutic intervention, it thus holds new promises in the fields of stem cell biology and regenerative medicine.

Induction of DE has been described by the use of Activin A/Nodal with or without the combination of Wnt. In particular, the Wnt receptor ligand Wnt3a has previously been reported to contribute to efficient DE formation when incubated along with activin A (AA) during day 1 (24 h) of a 5 day AA-mediated induction of DE, ie., using the conventional D'Amour protocol (Kroon et al 2008, Nat Biotech, 2006).

Attempts to group individual Wnt proteins into classes to which specific activities could be assigned have resulted in the subdivision of Wnts into 'canonical' or 'non-canonical', based on the ability of the former, but not the later, to induce beta-catenin/TCF signaling.

CHIR is a glycogen synthase kinase 3 beta (Gsk3b) inhibitor and a known component of a defined tissue culture medium to maintain mouse embryonic stem cells in the pluripotent state (Ying et al Nature 453, 519-523). Gsk3b has multiple targets but is mainly known to regulate degradation and/or nuclear transfer of beta-catenin. The role of stabilized beta-catenin in PS formation from human embryonic stem cells (hESC) has been described using other glycogen synthase kinase 3 beta (Gsk3b) inhibitors such as BIO and Wnt3a. However CHIR is the most selective Gsk3b-inhibitor reported to date.

Co-incubation of AA and CHIR reduces DE formation stability, leading to a less efficient and less robust protocol. The present invention relates to the utilization of CHIR without AA, at a defined concentration range to treat pluripotent stem cells prior to AA-mediated definitive endoderm induction compared to the conventional induction protocol for obtaining DE (D'Amour protocol, as described in Kroon et al. 2008). This sequential exposure, first to CHIR and then to AA, is essential and reflects successive PS formation (induced by CHIR) followed by more efficient and rapid DE formation by AA. The present invention relates to the discrete and successive control of induction of first PS then followed by DE leading to an overall more efficient, with earlier peak of SOX17 expression and robust DE protocol. These effects of CHIR cannot be reproduced with Wnt3a treatment.

DESCRIPTION OF THE DRAWINGS

D0: Undifferentiated cells before any treatment
Ctrl: No Chir treatment D1. Cells are left in RPMI during priming period, followed by AA D2 and AA+serum replacement (B27) from D3 onwards.
D'Am: No Chir treatment, protocol according to Kroon et al., Nat. Biotech., 2008 (1 day ActivinA 100 ng/ml+Wnt 25 ng/ml, 2 days ActivinA100 ng/ml+0.2% FBS)
D1: 1 day after Chir addition
D2-4: 1-3 d after AA addition
All gene expression graphs show Log10 values.

FIG. 4 shows hESC SA121 (4A-B) and iPSC chIPS4 (4C) cells treated with either CHIR (3 µM), BIO (0.5 µM), Wnt3a (200 ng/ml) or AA alone (100 ng/ml) for 24 h (D1) prior to 2 d AA treatment (D3). Additionally, D'Amour (protocol as described in Kroon et al 2008) was analyzed. Expression of Brachyury and SOX17 was analyzed. hES cells treated with AA or BIO for the first 24 h did not survive until day 3.

FIG. 6 shows gene expression of SOX17 D3 in hES SA121 (FIG. 6A) or chIPS4 (FIG. 6C) treated with either only RPMI, AA and Wnt3a or CHIR D1 followed by treatment with either AA or a combination of AA and Wnt3a D2 and AA D3 (FIG. 6A). Cells were also treated with either CHIR D1 and AA D2 ("CHIR"), D'Amour, or CHIR on top of D'Amour and were analyzed for SOX17 expression (FIG. 6B) and morphology (FIG. 6D).

FIG. 7 shows that CHIR was titrated at concentrations between 1-7 uM and analysed after 24 h (D1) and after 2 d of following AA treatment (D3). CHIR 0.5-1 uM and CHIR 7uM did not survive D3. Brachyury expression was analysed after 24 h treatment in SA121 (FIG. 7A) and chIPS cells (FIG. 7C). SOX17 expression was analysed D3 in SA121 (FIG. 7B) and chIPS cells (FIG. 7D)).

SUMMARY OF THE INVENTION

Figure 1:
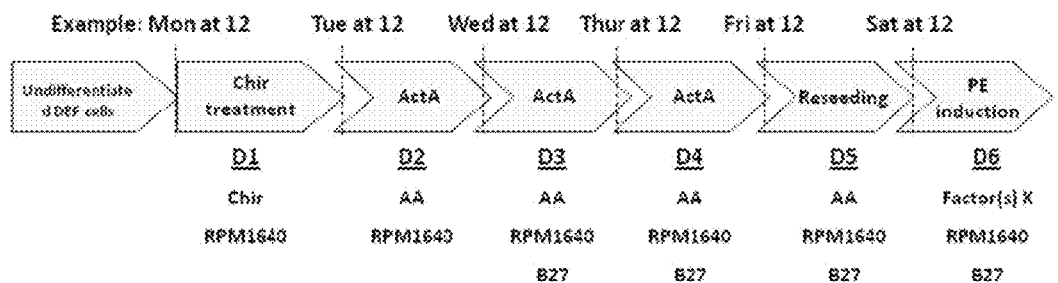
FIG. 1 shows the CHIR DEprotocol nomenclature and overview. The protocol has been confirmed in 7 different pluripotent stem cell lines: SA121, SA181, SA461, SA167 (human ESCs) and chIPS2, chIPS3, chIPS4 (human iPSCs).

The present invention also relates to a method for differentiation of stem cells into definitive endoderm comprising the steps of:
a. first priming step of incubating stem cells in a medium comprising at least 2 µM CHIR, wherein activin A is not present during said priming step; and
b. second subsequent step of incubating stem cells in a medium comprising activin A.

The present invention relates to a faster and more pronounced peak of SOX17 expression and a more robust method of differentiating human pluripotent stem cells to obtain definitive endoderm.

DESCRIPTION OF THE INVENTION

The present invention relates to a method for differentiation of stem cells into definitive endoderm comprising the steps of incubating pluripotent stem cells in a medium comprising at least 2 µM CHIR and subsequently incubating these cells in a medium comprising Activin A (AA).

The present inventors have found that using CHIR alone for 24 h prior to further addition of AA, induced a significant and dose dependent upregulation of PS markers such as Brachyury, Mixl1, Eomes and Goosecoid (GSC) during these 24 h.

The present inventors have surprisingly found that in the subsequent incubation with AA to induce DE, DE induction as measured by SOX17 expression, peaked at an earlier time point and with higher fold change when compared to cultures without CHIR pre-incubation or when compared to the conventional D'Amour protocol (Novocell, Nature Biotec 2006, 2008). The present inventors surprisingly found that the method of the present invention was more efficient and showed a faster induction of Sox17 mRNA expression than other known protocols for DE Induction.

The CHIR-mediated effect has been reproduced both in other culture systems (mTeSR media and conventional ES media on mouse embryonic feeder (MEF) cells) and across different cell lines (SA121, SA181, SA461, SA167, chIPS2, chIPS3, chIPS4), showing that the effect is not dependent on the cell line or the DEF media culture system. Human embryonic stem cells may be derived from single blastomeres without the destruction of the embryo (Klimanskaya et al. 2006; Chung et al. 2008; Geens et al. 2009). Cell lines chIPS2, chIPS3, chIPS4 are iPS cell lines.

The present inventors found that CHIR promotes high cell densities after AA is added. Dose dependency of CHIR in PS induction will allow future optimization of possible pre-patterning influences when initiating AA treatment. The subsequent order of added factors decreases the amount of signaling pathways that are activated in parallel. Minimizing the amount of factors that may influence the efficiency should promote robustness and reproducibility.

The present inventors have surprisingly found that the CHIR-priming step is unique for DE induction and was superior when compared to BIO or Wnt3a when it comes to efficiency peak of SOX17 expression and robustness.

Human embryonic stem cells (hESCs) and human induced pluripotent stem cells (iPSCs) from expandable pluripotent cultures were subjected to 24 h treatment of CHIR (2-7 µM) in plain RPMI-1640 medium. Following medium change to an AA containing RPMI-1640 medium, the DE induction commenced where SOX17 mRNA expression peaked after 2 days and SOX17 protein expression peaked after 3-4 days. Concentrations below 2 µM of CHIR caused a delayed induction of Brachyury to significantly lower levels and following subsequent AA stimulation the DE was not induced after 72 hrs. PS formation was delayed at CHIR concentrations under 1.5 µM thus disabling further progression toward DE when AA was added. The present inventors have surprisingly found that a concentration range greater or equal to 2 µM of CHIR for 24 hrs is important for the subsequent DE induction by AA.

The present inventors have surprisingly found the CHIR-priming step resulted in a remarkably fast induction of SOX17 by AA peaking already after 1 day which is in contrast to AA alone where the peak is seen only after 3-4 days. The sequential incubation with CHIR followed by AA is essential for DE formation to favourable levels.

Embodiments Of The Invention
1. A method for differentiation of stem cells into definitive endoderm comprising the steps of:
c. first priming step of incubating stem cells in a medium comprising at least 2 µM CHIR, wherein activin A is not present during said priming step; and
d. second subsequent step of incubating stem cells in a medium comprising activin A.

2. The method according to embodiment 1, wherein said medium is RPMI-1640.
3. The method according to any one of the preceding embodiments, wherein said stem cells are embryonic stem cells or induced pluripotent stem cells.
4. The method according to any one of the preceding embodiments, wherein said stem cells are embryonic stem cells.
5. The method according to embodiment 3, wherein said stem cells are human embryonic stem cells.
6. The method according to embodiment 3, wherein said stem cells are induced pluripotent stem cells.
7. The method according to any one of the preceding embodiments, wherein the concentration of CHIR is at least about 2.5 µM, or at least 3 µM, such as in a range of about 2-20 uM, such as in a range of about 3.1-15 µM, or such as in a range of about 3,5-7 µM or such as in a range of about 3.5-6 µM, or such as in a range of about 3.5-5 µM.
8. The method according to embodiment 7, wherein the concentration of CHIR is at least about 2 µM.
9. The method according to embodiment 7, wherein the concentration of CHIR is at least about 2.5 µM.
10. The method according to embodiment 7, wherein the concentration of CHIR is at least about 3 µM.
11. The method according to embodiment 7, wherein the concentration of CHIR is at least about 3.1 µM.
12. A method according to embodiment 7, wherein the concentration of CHIR is at least about 3.2 µM.
13. A method according to embodiment 7, wherein the concentration of CHIR is at least about 3.3 µM.
14. A method according to embodiment 7, wherein the concentration of CHIR is at least about 3.4 µM.
15. A method according to embodiment 7, wherein the concentration of CHIR is at least about 3.5 µM.
16. The method according to embodiment 7, wherein the concentration of CHIR is in the range of about 2-7 µM.
17. The method according to embodiment 7, wherein the concentration of CHIR is in the range of about 3-7 µM.
18. The method according to embodiment 7, wherein the concentration of CHIR is in the range of about 3.1-7 µM.
19. The method according to embodiment 7, wherein the concentration of CHIR is in the range of about 3.2-7 µM.
20. The method according to embodiment 7, wherein the concentration of CHIR is in the range of about 3.3-7 µM.
21. The method according to embodiment 7, wherein the concentration of CHIR is in the range of about 3.4-7 µM.
22. The method according to embodiment 7, wherein the concentration of CHIR is in the range of about 3.5-7 µM.
23. A method according to embodiment 7, wherein the concentration of CHIR is 2,5 µM.
24. A method according to embodiment 7, wherein the concentration of CHIR is 3 µM.
25. A method according to embodiment 7, wherein the concentration of CHIR is 3,1 µM.
26. A method according to embodiment 7, wherein the concentration of CHIR is 3,2 µM.
27. A method according to embodiment 7, wherein the concentration of CHIR is 3,3 µM.
28. A method according to embodiment 7, wherein the concentration of CHIR is 3,4 µM.
29. A method according to embodiment 7, wherein the concentration of CHIR is 3,5 µM.
30. A method according to embodiment 7, wherein the concentration of CHIR is 3,6 µM.
31. A method according to embodiment 7, wherein the concentration of CHIR is 3,7 µM.
32. A method according to embodiment 7, wherein the concentration of CHIR is 3,8 µM.
33. A method according to embodiment 7, wherein the concentration of CHIR is 3,9 µM.
34. A method according to embodiment 7, wherein the concentration of CHIR is about 4 µM.
35. A method according to embodiment 7, wherein the concentration of CHIR is about 4,5 µM.
36. A method according to embodiment 7, wherein the concentration of CHIR is about 5 µM.
37. A method according to any one of the preceding embodiments, wherein said incubation with CHIR is at least 12 hours.
38. A method according to any one of the preceding embodiments, wherein said incubation with CHIR is at least 24 hours.
39. A method according to any one of the preceding embodiments, wherein said incubation with CHIR is at least 48 hours.
40. A method according to embodiment 37, wherein said incubation with CHIR is between 24 and 48 hours.
41. A method according to embodiment 37, wherein said incubation with CHIR is 24 hours.
42. A method according to embodiment 37, wherein said incubation with CHIR is 48 hours.
43. The method according to any one of the preceding embodiments, wherein the concentration of activin A is at least about 100 ng/ml, such as in the range of about 1-5000 ng/ml, such as in the range of about 1-1000 ng/ml, such as in the range of about 10-500 ng/ml or such as in the range of about 1-200 ng/ml.
44. The method according to embodiment 43, wherein the concentration of activin A is in a range of about 1-200 ng/ml.
45. The method according to embodiment 43, wherein the concentration of activin A is in a range of about 20-200 ng/ml.
46. The method according to embodiment 43, wherein the concentration of activin A is in a range of about 30-200 ng/ml.
47. The method according to embodiment 43, wherein the concentration of activin A is at least 25 ng/ml.
48. The method according to embodiment 43, wherein the concentration of activin A is about 140 ng/ml.
49. The method according to embodiment 43, wherein the concentration of activin A is about 120 ng/ml.
50. The method according to embodiment 43, wherein the concentration of activin A is about 100 ng/ml.
51. The method according to embodiment 43, wherein the concentration of activin A is about 80 ng/ml.
52. The method according to embodiment 43, wherein the concentration of activin A is about 60 ng/ml.
53. The method according to embodiment 43, wherein the concentration of activin A is about 40 ng/ml.
54. A method according to any one of the preceding embodiments, wherein said incubation with activin A is in the range of 12 hours to 5 days, such as at least 12 hours, such as at least 24 hours or at least 48 hours, or such as 3-4 days.
55. A method according to embodiment 54, wherein said incubation with activin A is at least 12 hours.
56. A method according to embodiment 54, wherein said incubation with activin A is 24 hours.
57. A method according to embodiment 54, wherein said incubation with activin A is 48 hours.
58. A method according to embodiment 54, wherein said incubation with activin A is 72 hours.

59. A method according to embodiment 54, wherein said incubation with activin A is 48 to 72 hours.
60. A method according to embodiment 54, wherein said incubation with activin A is 3-4 days.
61. A method according to any one of the preceding embodiments, wherein endodermal cells are obtained from said definitive endoderm cells.
62. A method according to embodiment 61, wherein said endoderm cells are hepatic endoderm cells, pancreatic endoderm cells, intestinal endoderm cells and/or lung endoderm cells.
63. A method according to embodiment 62, wherein said endoderm cells are hepatic endoderm cells.
64. A method according to embodiment 62, wherein said endoderm cells are pancreatic endoderm cells.
65. Definitive endodermal cells obtainable by the methods of embodiments 1-64.
66. Endodermal cells obtainable by the methods of embodiments 1-64.
67. Hepatic endoderm cells, pancreatic endoderm cells, intestinal endoderm cells and/lung endoderm cells according to embodiment 66.
68. Endodermal cells according to embodiment 66, wherein said cells are hepatic endoderm cells.
69. Endodermal cells according to embodiment 66, wherein said cells are pancreatic endoderm cells.
70. The method according to embodiments 1-64, wherein beta-catenin is activated by CHIR-induced Gsk3b inhibition.
71. Use of CHIR in a concentration of CHIR in the culture medium is at least 2 µM CHIR, such as in the range of 3,1-15 µM, or such as 3,1-7 µM, or such as 3.5 -15 µM, or such as
72. Use of CHIR in a concentration of at least 3,1 µM in the culture medium, to induce primitive streak cells from embryonic stem cells.
73. Use of CHIR in a concentration in the range of 3,1-7 µM to induce definitive endoderm cells from embryonic stem cells.
74. Use of CHIR in a concentration in the range of 3,5-7 µM to induce definitive endoderm cells from embryonic stem cells.
75. Use of CHIR in a concentration of 3,5 µM to induce definitive endoderm cells from embryonic stem cells.
76. Use of CHIR in a concentration of 4 µM to induce definitive endoderm cells from embryonic stem cells.
77. Use of CHIR in a concentration of 4,5 µM to induce definitive endoderm cells from embryonic stem cells.
78. Use of CHIR in a concentration of 5 µM to induce definitive endoderm cells from embryonic stem cells.
79. Use according to embodiments 71-78, wherein said primitive streak expresses one or more of the following markers: Brachyury or Mixl1.
80. Use according to embodiments 71-78, wherein said definitive endoderm expresses one or more of the following markers Sox17.

Further embodiments of the present invention:
81. A method for differentiation of stem cells into definitive endoderm comprising the steps of:
    a. first priming step of incubating stem cells in a medium comprising at least 2 µM CHIR, wherein activin A is not present during said priming step; and
    b. second subsequent step of incubating stem cells in a medium comprising at least 25 ng/ml activin A.
82. A method for differentiation of stem cells into definitive endoderm comprising the steps of:
    a. first priming step of at least 12 hours, of incubating stem cells in a medium comprising at least 2 µM CHIR, wherein activin A is not present during said priming step; and
    c. second subsequent step of at least 12 hours, of incubating stem cells in a medium comprising at least 25 ng/ml activin A.
83. A method for differentiation of stem cells into definitive endoderm comprising the steps of:
    b. first priming step of at least 24 hours, of incubating stem cells in a medium comprising at least 2 µM CHIR, wherein activin A is not present during said priming step; and
    d. second subsequent step of at least 24 hours, of incubating stem cells in a medium comprising at least 25 ng/ml activin A.
84. A method for differentiation of stem cells into definitive endoderm comprising the steps of:
    a. first priming step of incubating stem cells in a medium comprising at least 3,1 µM CHIR, wherein activin A is not present during said priming step; and
    b. second subsequent step of incubating stem cells in a medium comprising at least 25 ng/ml activin A.
85. A method for differentiation of stem cells into definitive endoderm comprising the steps of:
    a. first priming step of incubating stem cells in a medium comprising at least 3,5 µM CHIR, wherein activin A is not present during said priming step; and
    b. second subsequent step of incubating stem cells in a medium comprising at least 25 ng/ml activin A.
86. The methods according to any one of the preceding embodiments, wherein said stem cells are embryonic stem cells or induced pluripotent stem cells.
87. The method according to embodiment 86, wherein said stem cells are human embryonic stem cells.
88. The method according to embodiment 86, wherein said stem cells are induced pluripotent stem cells.
89. The method according to any one of the preceding embodiments, wherein the concentration of CHIR is at least about 2, at least about 2.5 uM, at least about 3 uM, at least about 3.1 µM, such as in the range of about 3,1-15 µM, or such as about 3,5-7 µM or such as about 3.5-6 µM, or such as about 3,5-5 µM.
90. The method according to any one of the preceding embodiments, wherein the concentration of CHIR is at least about 3,1 µM.
91. A method according to any one of the preceding embodiments, wherein the concentration of CHIR is at least about 3,2 µM.
92. A method according to any one of the preceding embodiments, wherein the concentration of CHIR is at least about 3,3 µM.
93. A method according to any one of the preceding embodiments, wherein the concentration of CHIR is at least about 3,4 µM.
94. A method according to any one of the preceding embodiments, wherein the concentration of CHIR is at least about 3,5 µM.
95. The method according to any one of the preceding embodiments, wherein the concentration of CHIR is in the range of about 3,1-7 µM.
96. The method according to any one of the preceding embodiments, wherein the concentration of CHIR is in the range of about 3,2-7 µM.
97. The method according to any one of the preceding embodiments, wherein the concentration of CHIR is in the range of about 3,3-7 µM.

98. The method according to any one of the preceding embodiments, wherein the concentration of CHIR is in the range of about 3,4-7 µM.
99. The method according to any one of the preceding embodiments, wherein the concentration of CHIR is in the range of about 3,5-7 µM.
100. A method according to any one of the preceding embodiments, wherein said incubation with CHIR is at least 24 hours.
101. A method according to any one of the preceding embodiments, wherein said incubation with CHIR is at least 48 hours.
102. A method according to any one of the preceding embodiments, wherein said incubation with CHIR is between 24 and 48 hours.
103. A method according to any one of the preceding embodiments, wherein said incubation with CHIR is 24 hours.
104. A method according to any one of the preceding embodiments, wherein said incubation with CHIR is 48 hours.
105. The method according to any one of the preceding embodiments, wherein the concentration of activin A is in a range of about 25-200 ng/ml.
106. A method according to any one of the preceding embodiments, wherein the concentration of activin A is in a range of about 30-200 ng/ml.
107. The method according to any one of the preceding embodiments, wherein the concentration of activin A is about 100 ng/ml.
108. The method according to any one of the preceding embodiments, wherein the concentration of activin A is about 80 ng/ml.
109. The method according to any one of the preceding embodiments, wherein the concentration of activin A is about 60 ng/ml.
110. The method according to any one of the preceding embodiments, wherein the concentration of activin A is about 40 ng/ml.
111. The method according to any one of embodiments, wherein the concentration of activin A is at least about 110 ng/ml.
112. A method according to any one of the preceding embodiments, wherein said incubation with activin A is in the range of 12 hours to 5 days, such as at least 12 hours, such as at least 24 hours or at least 48 hours, or such as 3-4 days.
113. A method according to any one of the preceding embodiments, wherein said incubation with activin A is at least about 24 hours.
114. A method according to any one of the preceding embodiments, wherein said incubation with activin A is about 24 hours.
115. A method according to any one of the preceding embodiments, wherein said incubation with activin A is about 48 hours.
116. A method according to any one of the preceding embodiments, wherein said incubation with activin A is about 72 hours.
117. A method according to any one of the preceding embodiments, wherein said incubation with activin A is about 48 to about 72 hours.
118. A method according to any one of the preceding embodiments, wherein said incubation with activin A is about 3-4 days.
119. A method according to any one of the preceding embodiments, wherein endodermal cells are obtained from said definitive endoderm cells.
120. A method according to embodiment 119, wherein said endoderm cells are hepatic endoderm cells, pancreatic endoderm cells, intestinal endoderm cells and/or lung endoderm cells.
121. A method according to embodiment 120, wherein said endoderm cells are hepatic endoderm cells.
122. A method according to embodiment 120, wherein said endoderm cells are pancreatic endoderm cells.
123. Definitive endodermal cells obtainable by the methods of embodiments 81-122.
124. Endodermal cells obtainable by the methods of embodiments 81-122.
125. Hepatic endoderm cells, pancreatic endoderm cells, intestinal endoderm cells and/lung endoderm cells according to embodiment 124.
126. Endodermal cells according to embodiment 124, wherein said cells are hepatic endoderm cells.
127. Endodermal cells according to embodiment 124, wherein said cells are pancreatic endoderm cells.
128. The method according to embodiments 81-122, wherein beta-catenin is activated by CHIR-induced Gsk3b inhibition.
129. Use of CHIR in a specific concentration to induce primitive streak cells from stem cells.
130. Use of CHIR in a specific concentration to induce definitive endoderm cells from stem cells.
131. Use according to embodiments 129-130, wherein the concentration of CHIR in the culture medium is at least 2 µM CHIR.
132. Use according to embodiments 129-131, wherein the concentration of CHIR in the culture medium is at least 2µM CHIR, such as in the range of 2-7 µM, such as 3 µM or such as 4 µM.
133. Use of CHIR in a concentration in the range of 2-7 µM to induce definitive endoderm cells from embryonic stem cells.
134. Use of CHIR in a concentration in the range of 3-7 µM to induce definitive endoderm cells from embryonic stem cells.
135. Use of CHIR in a concentration in the range of 3,5-7 µM to induce definitive endoderm cells from embryonic stem cells.

In one embodiment, the pancreatic endocrine cells obtainable by the method according to the invention are insulin producing cells, optionally together with cells differentiated towards glucagon, somatostatin, pancreatic polypeptide, and/or ghrelin producing cells. As used herein, "insulin producing cells" refers to cells that produce and store or secrete detectable amounts of insulin. "Insulin producing cells" can be individual cells or collections of cells.

In another embodiment, the cell population comprising pancreatic cells is obtained from a somatic cell population. In some aspects the somatic cell population has been induced to de-differentiate in to an embryonic-like stem (ES, e.g., a pluripotent) cell. Such dedifferentiated cells are also termed induced pluripotent stem cells (IPS).

In another embodiment, the cell population comprising pancreatic cells is obtained from embryonic stem (ES, e.g., pluripotent) cells. In some aspects the cell population comprising pancreatic cells is pluripotent cells such as ES like-cells.

In another embodiment, the cell population comprising pancreatic cells is embryonic differentiated stem (ES or pluripotent) cells. Differentiation takes place in embryoid bodies and/or in monolayer cell cultures or a combination thereof.

In another embodiment, the cell population is a population of stem cells. In some aspects the cell population is a population of stem cells differentiated to the pancreatic endocrine lineage.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multi-potent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multi-potent stem cells; and (5) unipotent, meaning able to give rise to a single cell lineage (e.g., spermatogenic stem cells).

A protocol for obtaining pancreatic cells from stem cells is exemplified by, but not limited to, the protocols described in D'Amour, K. A. et al. (2006), Nat Biotechnol 24, 1392-401; Jiang, J. et al. (2007), Stem Cells 25, 1940-53; and Kroon, E. et al. (2008), Nat Biotechnol 26, 443-452.

A protocol for obtaining pancreatic cells from somatic cells or somatic cells induced to de-differentiate into pluripotent cells such as ES like-cells is exemplified by, but not limited to, the protocols described in Aoi, T. et al. (2008), Science 321(no. 5889), 699 - 702; D'Amour, K. A. et al. (2006), Nat Biotechnol 24, 1392-401; Jiang, J. et al. (2007), Stem Cells 25, 1940-53; Kroon, E. et al. (2008), Nat Biotechnol 26, 443-452; Takahashi, K. et al. (2007), Cell 131, 861-72; Takahashi, K., and Yamanaka, S. (2006), Cell 126, 663-76; and Wernig, M. et al. (2007), Nature 448, 318-24.

As used herein "differentiate" or "differentiation" refers to a process where cells progress from an undifferentiated state to a differentiated state, from an immature state to a less immature state or from an immature state to a mature state. For example, early undifferentiated embryonic pancreatic cells are able to proliferate and express characteristics markers, like Pdx1, Nkx6.1, and Ptf1a. Mature or differentiated pancreatic cells do not proliferate and do secrete high levels of pancreatic endocrine hormones or digestive enzymes. E.g., fully differentiated beta cells secrete insulin at high levels in response to glucose. Changes in cell interaction and maturation occur as cells lose markers of undifferentiated cells or gain markers of differentiated cells. Loss or gain of a single marker can indicate that a cell has "matured or fully differentiated." The term "differentiation factor" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like peptide 1. In some aspects differentiation of the cells comprises culturing the cells in a medium comprising one or more differentiation factors.

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in 30 literature often denoted as human embryonic stem (hES) cells, (see, e.g., Thomson et al. (1998), Heins et. al. (2004), as well as induced pluripotent stem cells (see, e.g. Yu et al., (2007) Science 318:5858); Takahashi et al., (2007) Cell 131(5):861). The various methods and other embodiments described herein may require or utilise hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein "hiPS cells" refers to human induced pluripotent stem cells.

As used herein, the term "blastocyst-derived stem cell" is denoted BS cell, and the human form is termed "hBS cells". In literature the cells are often referred to as embryonic stem cells, and more specifically human embryonic stem cells (hESC). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent cells by e.g. the treating adult cells with certain transcription factors, such as OCT4, SOX2, NANOG, and LIN28 as disclosed in Yu, et al., 2007, Takahashi et al. 2007 and Yu et al 2009.

As used herein "feeder cells" are intended to mean supporting cell types used alone or in combination. The cell type may further be of human or other species origin. The tissue from which the feeder cells may be derived include embryonic, fetal, neonatal, juvenile or adult tissue, and it further includes tissue derived from skin, including foreskin, umbilical chord, muscle, lung, epithelium, placenta, fallopian tube, glandula, stroma or breast. The feeder cells may be derived from cell types pertaining to the group consisting of human fibroblasts, fibrocytes, myocytes, keratinocytes, endothelial cells and epithelial cells. Examples of specific cell types that may be used for deriving feeder cells include embryonic fibroblasts, extraembryonic endodermal cells, extraembryonic mesoderm cells, fetal fibroblasts and/or fibrocytes, fetal muscle cells, fetal skin cells, fetal lung cells, fetal endothelial cells, fetal epithelial cells, umbilical chord mesenchymal cells, placental fibroblasts and/or fibrocytes, placental endothelial cells, As used herein, the term "MEF cells" is intended to mean mouse embryonic fibroblasts.

As used herein, "CHIR", "Chir" or "Chir99021", is a patented commercially available glycogen synthase kinase 3 beta (Gsk3b) inhibitor covered in patent U.S. Pat. No.

6,417,185 and described by Goff, D. A., et al. (2002) Inhibitors of glycogen synthase kinase 3.

Embodiments of the present invention:
136. A method for differentiation of stem cells into definitive endoderm comprising the steps of:
   a. incubating stem cells in a medium comprising at least 2 µM CHIR; and
   b. subsequently incubating stem cells in a medium comprising activin A.
137. A method according to embodiment 136, wherein activin A is not present during said incubation with CHIR.
138. A method according to embodiments 136-137, wherein said medium is RPMI-1640.
139. A method according to any of embodiments 136-138, wherein said stem cells are embryonic stem cells.
140. A method according to any of embodiments 136-139, wherein the concentration of CHIR is at least 2 µM, such as in the range of 2-7 µM, or such as 3 µM or such as 4 µM.
141. A method according to any of embodiments 136-140, wherein said incubation with CHIR is at least 12 hours, such as 24 hours.
142. A method according to any of embodiments 136-141, wherein said incubation with activin A is in the range of 12 hours to 5 days, such as at least 12 hours, such as at least 24 hours or at least 48 hours, or such as 3-4 days.
143. A method according to any of embodiments 136-142, wherein specific endodermal cells are obtained from said definitive endoderm cells.
144. A method according to embodiment 143, wherein said specific endoderm cells are pancreatic endoderm cells.
145. Definitive endodermal cells obtainable by the methods of embodiment 136-144.
146. Specific endodermal cells obtainable by the methods of embodiment 136-145.
147. Use of CHIR in a specific concentration to induce primitive streak cells from stem cells.
148. Use of CHIR in a specific concentration to induce definitive endoderm cells from stem cells.
149. Use according to embodiments 147-148, wherein the concentration of CHIR in the culture medium is at least 2 µM CHIR.
150. Use according to embodiments 147-148, wherein the concentration of CHIR in the culture medium is at least 2µM CHIR, such as in the range of 2-7 µM, such as 3 µM or such as 4 µM.
151. Use of CHIR in a concentration in the range of 2-7 uM to induce definitive endoderm cells from embryonic stem cells.
152. Use of CHIR in a concentration in the range of 3-7 uM to induce definitive endoderm cells from embryonic stem cells.
153. Use of CHIR in a concentration in the range of 3,5-7 uM to induce definitive endoderm cells from embryonic stem cells.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

ABBREVIATIONS

AA: Activin A
D'Am: D'Amour protocol (Kroon et al., 2008)
DE: definitive endoderm
bFGF: basic fibroblast growth factor (FGF2)
Gsk3b: glycogen synthase kinase 3 beta
hBSC: human blastocyst-derived stem cells
hESC: human embryonic stem cells
hIPSC: human induced pluripotent cells
hPSC: human pluripotent stem cells
KO-SR: knockout serum replacement
RNA: ribonucleic acid
PCR: polymerase chain reaction
PS: primitive streak
SOX17: SRY (sex determining region Y)-box 17
T: Brachyury

EXAMPLES

Example 1

In Vitro Culture of Human ES/iPS Cells

The DE protocol was confirmed in two different feeder free (DEF, mTeSR) culture systems and one feeder dependent (MEF-ES) culture system.

DEF hESC/iPS Culture System

Human embryonic stem (hES) cells SA121 and chIPS4 (Cellartis) were grown on human fibronectin (Sigma) in DEF culture media (Cellartis) with 30 ng/ml bFGF (Invitrogen) and 10 ng/ml Noggin (Peprotech) in 6-96 well plates. Cells were single cell passaged with Rock inhibitor Y-27632 (Calbiochem) and seeded at a density of 40000 cells/cm2 for experiments. Experiments were initiated 4 d after passage.

mTeSR Culture System hES cells (SA121) were cluster passaged from feeders (MEFs) to Matrigel (BD Biosciences) in mTeSR1 media (Cell Signaling Techologies) and passaged further with Dispase (BD Biosciences) according to the culture system protocol. DE was initiated once clusters started to touch each other

MEF-ES hES cells (SA121) were passaged on gelatine-coated plates pre-seeded with MEFs in hES media (KO-DMEM, PEST, Glutamax, NEAA, 2-mercaptoethanol, KO serum replacement, 10 ng/ml bFGF). DE was initiated at 80% confluency.

Example 2

CHIR DE Protocol

Confluent cultures were washed once in RPMI1640 (Invitrogen) before 24 hour pre-treatment with 0,5-7µM CHIR99021 (Stemgent) in RPMI. Control cells were left untreated in RPMI and D'Amour cells were either left in RPMI or treated with AA (Peprotech)+Wnt3a (R&D Systems) without pre-treatment depending on experimental setup.

After 24 hours, pretreated and control cells were washed once with RPMI before adding 100 ng/ml AA in RPMI. D'Amour cells were also treated with 100 ng/ml AA but with 0,2% FBS instead of B27. 24 h later, 2% B27 (Invitrogen) was added to the AA media for 2-3 d. Control cells were treated with B27 to prevent cell death and D'Amour cells with 2% FBS according to published protocol. Media was changed every day.

When cells were further differentiated to PE, the DE protocol was applied in T75 cell culture flasks and reseeded after 4 d of DE culture at a density of 200 K in DE media. 1 d later, cells were washed once before addition of PE media (RPMI1640+12% KOSR+64 ng/ml bFGF) according to published protocol (Amen et al 2010).

Overview of the CHIR Definitive Endoderm protocol can be found in FIG. 1. The protocol has been confirmed in 7 different cell lines: SA121, SA181, SA461, SA167 (hESC) and chIPS2, chIPS3, chIPS4 (hiPSC).

TABLE 1

CHIR DE cell culture protocol

| | Ctrl | CHIR protocol | D'Amour |
|---|---|---|---|
| Day 1 medium | RPMI1640 0.1% PEST | CHIR99021, 3 uM RPMI1640 0.1% PEST | Activin A (AA) 100 ng/ml Wnt3a 25 ng/ml RPMI1640 0.1% PEST |
| Day 2 medium | Activin A (AA) 100 ng/ml RPMI1640 0.1% PEST | Activin A (AA) 100 ng/ml RPMI1640 0.1% PEST | Activin A (AA) 100 ng/ml RPMI1640 0.2% FBS 0.1% PEST |
| Day 3 medium | Activin A (AA) 100 ng/ml RPMI1640 2% B27 0.1% PEST | Activin A (AA) 100 ng/ml RPMI1640 2% B27 0.1% PEST | Activin A (AA) 100 ng/ml RPMI1640 0.2% FBS 0.1% PEST |

Day 1: Cells were washed carefully in prewarmed (37° C.) RPMI before starting the differentiation. Day1 medium was premixed (CHIR 3 µM in prewarmed RPMI+PEST) and gently added to cell culture. Volumes were adjusted according to plate formats.

Day 2: Cells were washed carefully in prewarmed (37° C.) RPMI before media change. Day2 medium was premixed (100 ng/ml Activin A in prewarmed RPMI+0.1% PEST) and gently added to cell culture.

Day 3: Day3&4 mediums were premixed (100 ng/ml Activin A and 2% B27 in prewarmed RPMI+0.1% PEST) and gently added to cell culture.

Day 4: DE was harvested or reseeded for further differentiation. Cells were checked under the microscope every day.

Example 3

RNA Extraction and Quantitative Real-Time PCR

RNA samples were collected after 24 h pre-treatment (D1), after 1 day of AA treatment (D2) and after 1-2 d of AA+B27 treatment (D3-4). Total RNA was extracted with the Rneasy Plus Mini kit (Qiagen) and quantitative real-time PCR was performed using the StepOnePLus system (Applied Biosystems).

ICC Staining Procedure

Cells were washed in PBS+/+ and fixed in 4% formaldehyde for 30 min (10% formaline, VWR). The cells were then washed again three times in PBS and left in PBS (4° C.) until staining. Fixed cells were washed with PBS once, then permeabilized with 0.5% Triton X-100 in PBS for 6 min, washed in PBS and blocked with TNB buffer (0.1 M Tris-HCL pH 7.5, 0.15 M NaCl, 0.5% Blocking Reagent (Perkin Elmer)) for 30 min. Primary antibodies (goat-anti-SOX17 (AF1924, RnD Systems); goat-anti-Brachyury (AF2085, RnD Systems); mouse-anti-OCT4 (sc5279, SantaCruz Biotechnology); goat-anti-PDX1 (AB47383, Abcam)) were added in 0.1% TritonX-100+PBS for 1 h in RT or 4° C. O/N. After a thorough washing step in PBS, secondary antibodies were added together with DAPI in 0.1% Triton X-100+PBS for 45 min at RT, washed thoroughly in PBS and left in PBS until photodocumentation.

Example 4

Speed and Efficiency

Figure 2A:
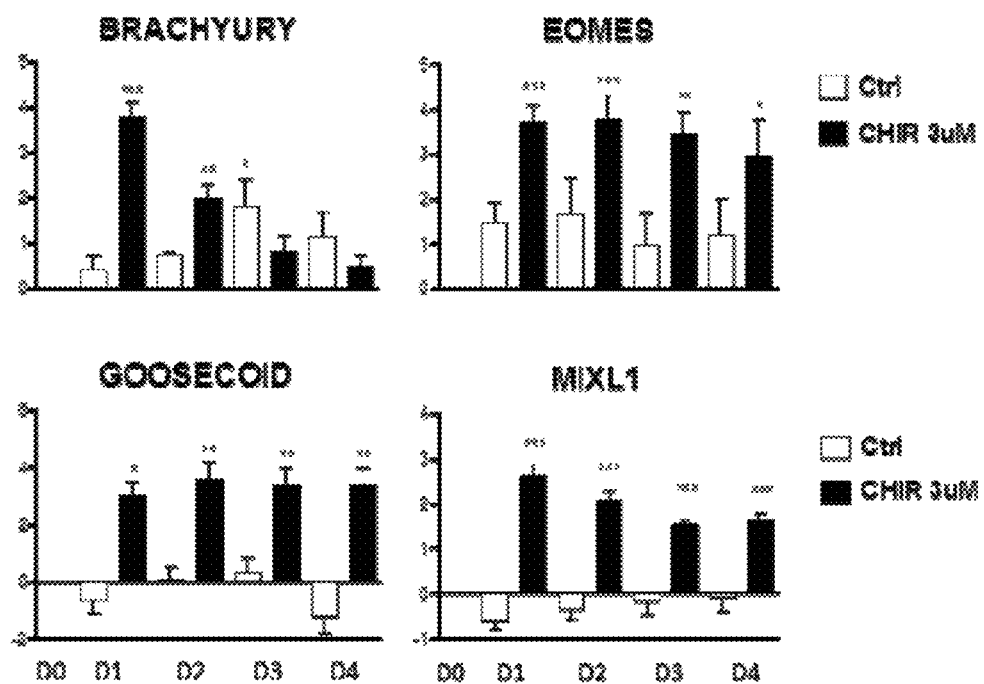
FIG. 2 shows transcriptional expression of PS markers Brachyury (T), MIXL1, EOMES and Goosecoid (GSC) after 24 h of CHIR treatment (D1) in hES SA121 (FIG. 2A) and chIPS4 (FIG. 2B), compared to non-treated cells. T protein levels were also confirmed with ICC (FIG. 2C). T fold inductions after 24 h CHIR treatment have spanned between 500-100000 compared to undifferentiated cells (n>60). Bars show Log10 values relative to undifferentiated cells D0.
Figure 2B:
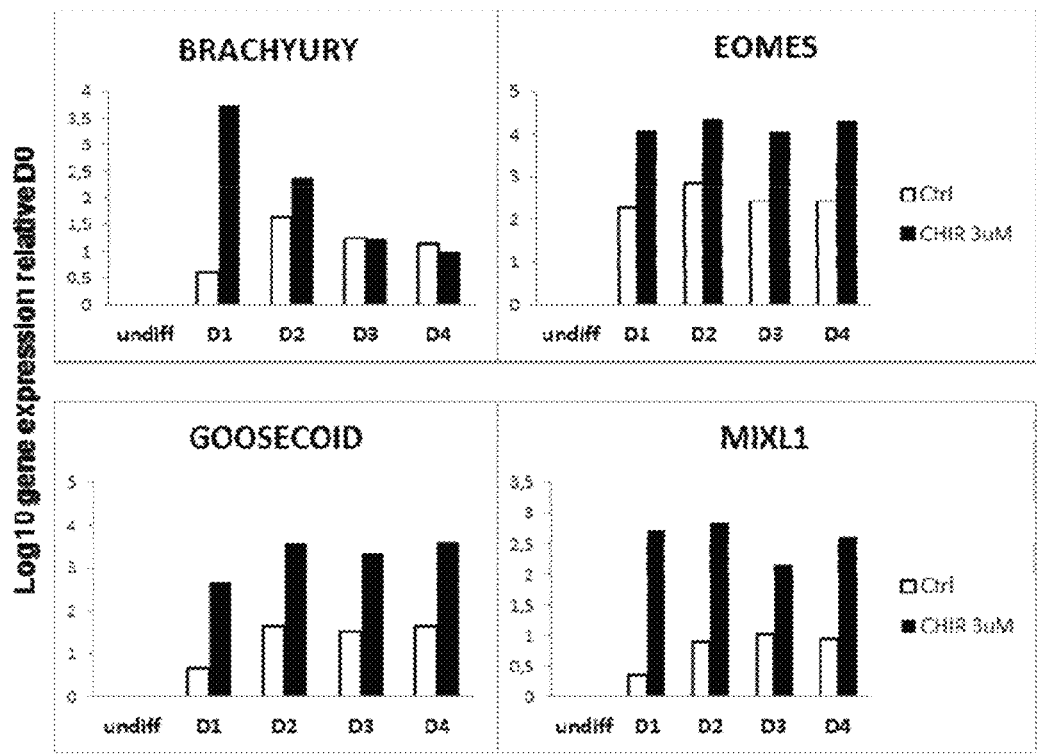
Figure 2C:
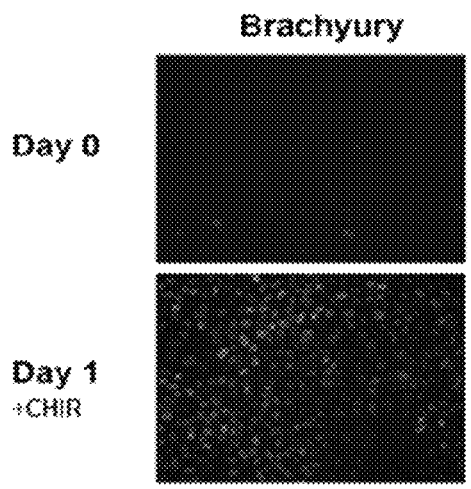

Undifferentiated SA121 hES and chIPS4 iPS cells in DEF media (D0) were cultured either in RPMI without CHIR (Ctrl D1) or treated for 24 h with CHIR in RPMI (CHIR D1). The cells were then washed to ensure absence of CHIR and then both conditions were treated with 1 d AA (Ctrl and CHIR d2). After 1 d CHIR treatment, PS markers such as Brachyury (T), MIXL1, EOMES and GSC were highly upregulated compared to non pre-treated cells (FIG. 2A-C). T fold inductions after 24 h CHIR treatment spanned between 500-100000 compared to undifferentiated cells (d0). T protein levels were also confirmed with ICC (FIG. 2C).

Figure 3A:
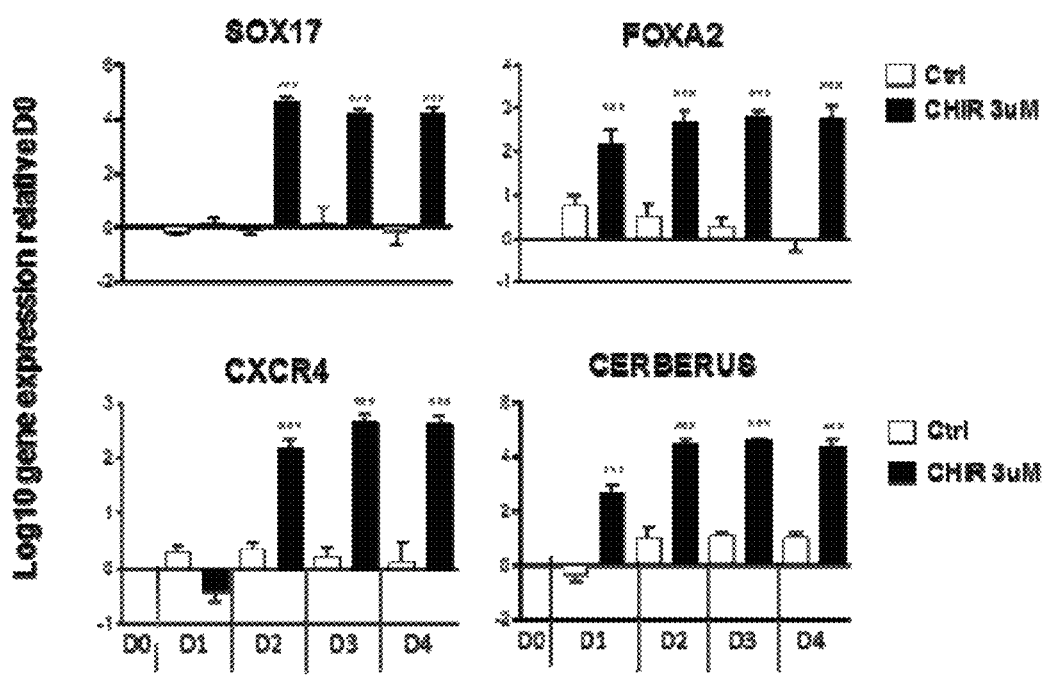
FIG. 3 shows gene expression of DE markers (SOX17, CXCR4, FOXA2, CER) one day after replacing CHIR with Activin A (AA) compared to with cells that were not pretreated with CHIR. Expression is shown both in hESC SA121 (FIG. 3A) and iPSC chIPS4 (FIG. 3B). Bars show Log10 values relative to undifferentiated cells D0.
Figure 3B:
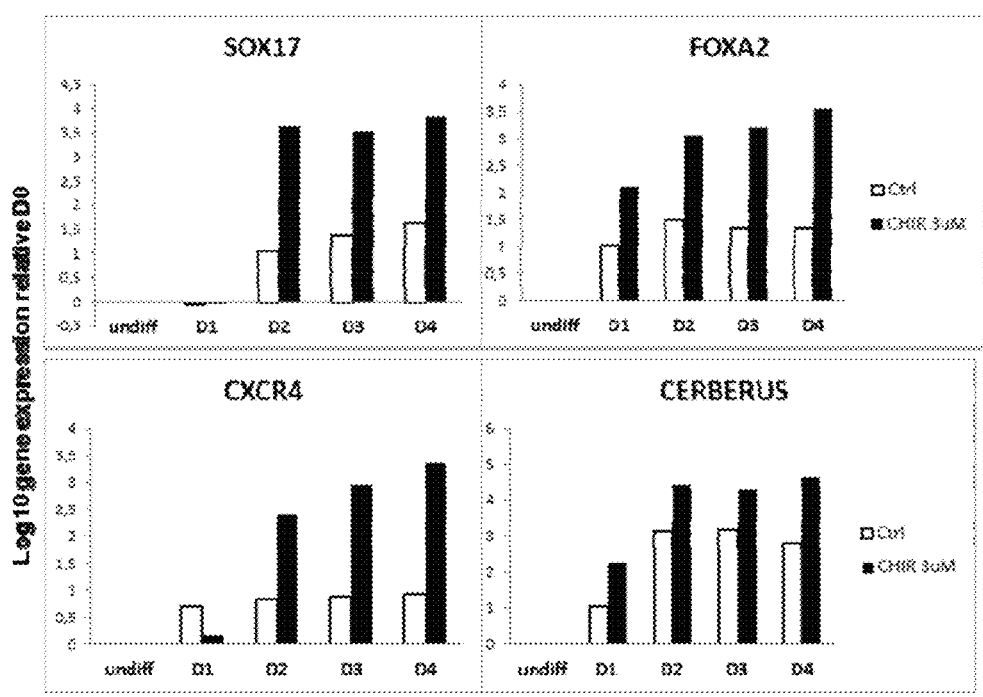

1 d after AA addition (D2), markers that together are indicative of DE formation such as SOX17, CXCR4, FOXA2 and CER were also highly upregulated compared to non-pre-treated cells despite addition of AA to both conditions (FIG. 3A,B), Sox17-fold inductions after CHIR pre-treatment spanned between 10000-3500000 compared to undifferentiated cells (D0, n>60). The efficiency levels for both T and SOX17 were highly robust (n>60) and confirmed with IHC and SOX17 quantifications (FIG. 2C and Table 2.). The CHIR pre-treatment step resulted in a remarkably rapid induction of SOX17 after AA treatment. SOX17 expression peaked already after one day of AA treatment when cells were subjected to CHIR for 24 h before AA induction. Cells in AA-containing media that were not pre-treated with CHIR (ctrl) did not show same speed or efficiency in Sox17 induction.

CHIR has a direct capacity to induce PS markers after 24 h treatment (D1) and resulted in a remarkably higher ability for AA to induce DE when added (D2). Brachyury was greatly repressed once AA was added indicating that the cells were differentiating in a highly stepwise order.

TABLE 2

| | OCT4 and SOX17 protein ICC quantifications in undifferentiated hES SA121/chIPS4 cells | | | | | | | |
|---|---|---|---|---|---|---|---|---|
| | OCT4 | | | | SOX17 | | | |
| | SA121 | | chIPS4 | | SA121 | | chIPS4 | |
| ICC % | D'Amour | CHIR | D'Amour | CHIR | D'Amour | CHIR | D'Amour | CHIR |
| Undiff | 97.5 | | 98.3 | | 0 | | 0 | |
| D1 | 91.9 | 97.7 | 94.3 | 91.2 | 0 | 0 | 8.3 | 0.9 |
| D2 | 55.2 | 2.4 | 14 | 3.1 | 61.6 | 72.1 | 75.2 | 68.8 |
| D3 | 44.1 | 0.2 | 26.2 | 3.7 | 80.4 | 93.1 | 77.6 | 91.5 |

Table 2 shows D1-3 of DE induction according to D'Amour (protocol as described in Kroon et al 2008) and cells treated with 3 µM CHIR (CHIR D1) prior to addition of ActivinA (CHIR D2-3).

Example 5

CHIR Specificity hES SA121 and ChIPS4 cells were treated with either CHIR (3 µM), BIO (0.5 µM), Wnt3a (200 ng/ml) or AA alone (100 ng/ml) for 24 h prior to AA addition to show CHIR specificity (d1). Additionally, D'Amour (protocol as described in Kroon et al 2008) was tested in parallel.

CHIR treatment significantly upregulated Brachyury expression after 24 h (FIG. 4A,C). After AA addition (D2), Brachyury was reduced and SOX17 was upregulated (FIG. 4B). hES cells treated with AA or BIO did not survive until day 3.

The data clearly illustrated that PS transition (upregulation of Brachyury) and DE induction (upregulation of SOX17) were both accelerated and much higher after CHIR treatment compared to pretreatment with growth factors such as AA and Wnt3a. Pretreatment of the cells with another small molecule Gsk3b inhibitor (BIO) did not elicit the same effect and the cells did not survive until d3. Treatment with either Wnt3a and BIO instead of CHIR delayed the Brachyury (PS) response (upregulated D2) compared to CHIR treatment (data not shown). Furthermore, these substances induced both Brachyury and SOX17 gene expression with significantly lower efficiency and cells treated with AA or BIO did not survive until d3. This protocol was also highly superior to the previously published D'Amour protocol.

Example 6

CHIR vs. D'Amour Protocol (DE and PE Induction)

Undifferentiated ChIPS4 cells (d0) were either pre-treated for 24 h with CHIR (3 µM) or directly exposed to AA (100 ng/ml) and Wnta3a (25 ng/ml) according to Kroon et al 2008. The cells were then washed and AA was added for 1-4 d. See Table 1 for detailed setup.

Figure 5:
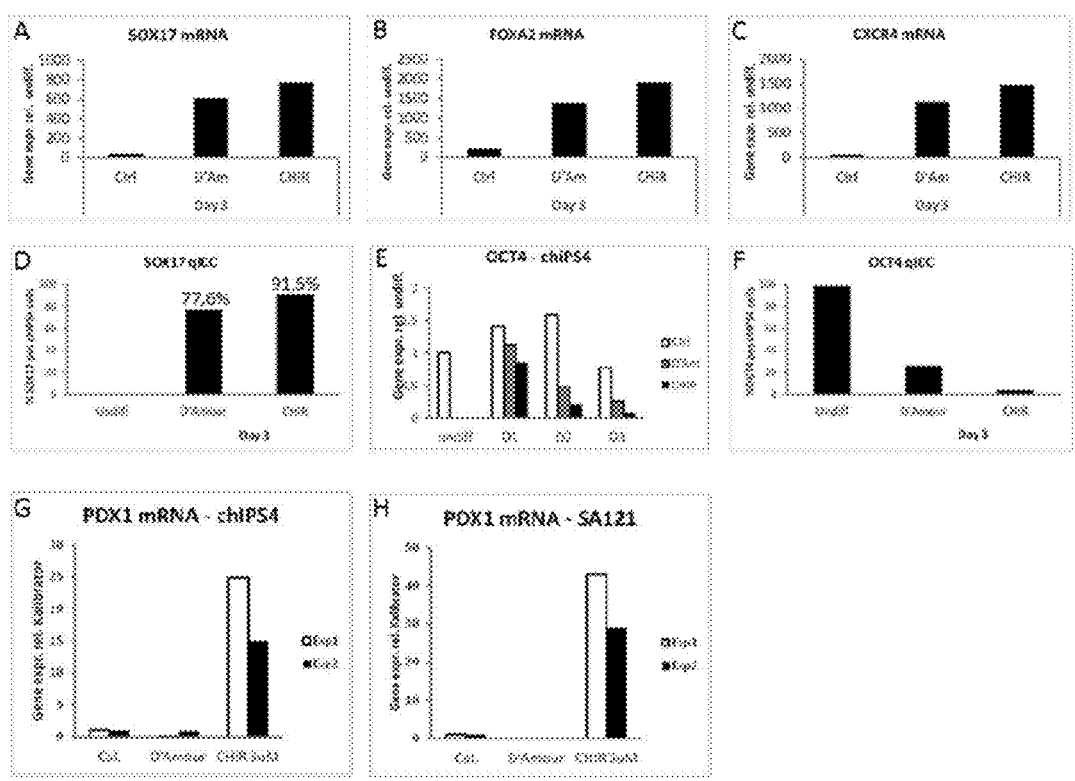
FIG. 5 shows gene expression levels of DE markers SOX17, FOXA2 and CXCR4 (FIG. 5A-C) and OCT4 (FIG. 5E) after CHIR induction compared to D'Amour and quantified ICC protein levels of SOX17/OCT4 in chIPS4 cells (FIG. 5D, F). Corresponding % of cells positively stained for OCT4 and SOX17 (D1-3) are also indicated in Table 2. chIPS/SA121 DE cells, using either of the two protocols, were further differentiated towards pancreatic endoderm (PE) using a previously published PE differentiation protocol (Amen et al 2010). Cells were analyzed after seven days of PE induction using ICC for PDX1 protein levels. In parallel, mRNA was collected from the cells and the PDX1 expression was analyzed by real-time PCR for both chIPS4 cells (FIG. 5G) and SA121 cells (FIG. 5H). The experiment was repeated twice in both cell lines (FIG. 5G, H).

CHIR treatment was superior in upregulating both T (mRNA D1) and SOX17 after CHIR pre-treatment (mRNA, ICC D3) compared to D'Amour (FIG. 5 and Table 2). In addition, the most striking difference between the protocols could be seen in terms of morphology with a much higher degree of cell death during D'Amour treatment. To further strengthen the results, a quantification of SOX17 protein expression was thus performed. chIPS4 cells treated with either the CHIR- or D'Amour-protocol were fixed and stained using a SOX17-specific ab and the images were quantified in respect of total amounts and the percentage of SOX17-positive cells. As shown in FIG. 6D, 91.5% of the CHIR-treated cells were found to be positive for SOX17 whereas only 77.6% of the D'Amour-treated cells showed SOX17 positive staining d3. In addition, the total amount of CHIR pre-treated cells was 25% higher than the number seen after D'Amour treatment.

The decrease of OCT4 expression was also analyzed in chIPS4 cells using both qPCR and qICC. The data clearly shows that the CHIR-protocol is more sufficient in reducing OCT4 expression at both mRNA and protein levels (FIG. 5E, F).

To further compare the efficiency between the CHIR- and D'Amour protocols, chIPS4 cells differentiated to DE, using either of the two protocols, were further differentiated towards pancreatic endoderm (PE) by using a previously published PE differentiation protocol (Ameri et al 2010). Seven days after the induction of PE differentiation the cells were fixed and analyzed by ICC using a PDX1 specific antibody. The results showed very modest PDX1-staining in the D'Amour-treated cells whereas the staining was evident in the CHIR pre-treated cells (data not shown). In parallel, mRNA was collected from the cells and the PDX1 expression was analyzed by real-time PCR. Concordantly with the ICC results, almost no PDX1 mRNA expression was found in D'Amour-treated cells while a clear expression was seen in the CHIR-differentiated cells (FIG. 5G). The experiment was repeated twice in both cell lines (FIG. 5G,H).

Example 7

Timing

Cells were pre-treated 1 d with either RPMI (ctrl), CHIR 3 uM, CHIR 3 uM+AA 100 ng/ml or 100 ng/ml AA+25 ng/ml Wnt3a (D'Amour) prior to addition of AA+/−Wnt3a (25 ng/ml) d2 and AA d3 (Table 3). B27 was added in Ctrl and CHIR d3 and FBS to D'Amour d2-3.

TABLE 3

| Protocols used for DE induction | | | |
|---|---|---|---|
| Condition | D1 | D2 | D3 |
| Ctrl | RPMI | AA | AA + B27 |
| D'Amour | AA + Wnt3a | AA + FBS | AA + FBS |
| DE prot | CHIR | AA | AA + B27 |
| DE prot + Wnt d2 | CHIR | AA + Wnt3a | AA + B27 |
| CHIR + AA | CHIR + AA | AA | AA + B27 |

The data shows that absence of Wnt3a after CHIR treatment does not affect SOX17 induction negatively (FIG. 6A, C). However, AA exclusion after CHIR treatment maintained Brachyury expression (data not shown) and limited further progression toward DE.

Adding AA on top of CHIR during pre-treatment did not show additive effects, the protocol stability was however negatively affected with high inter-experimental variation in terms of DE induction. A negative effect on cell survival D1 was also often seen when combining CHIR and AA during pretreatment (see cell morphology D1, FIG. 6D), Adding CHIR on top of D'Amour D1 also showed reduced SOX17 expression D2 compared to cells pretreated with CHIR (FIG. 6B).

CHIR pretreatment replaces the requirement of both Wnt3a and AA during the first day of differentiation toward DE and also has a stabilizing effect leading to a more robust protocol.

CHIR and exogenous AA may have counteracting effects that reduce overall efficiency and/or target different cell populations differently, resulting in higher levels of heterogeneity within the cell culture and increased inter-experimental variability. This suggests that PS induction/transition before adding AA to the media is an important and novel step to enhance protocol efficiency and robustness.

Example 8

Dose Dependency

Chir was titrated at concentrations between 1-7 uM and analyzed after 24 h Chir treatment (D1) and after 2 d of following AA treatment (D3). CHIR 0.5-1 uM and CHIR 7 uM did not survive d3.
  1. After 24 h treatment, Brachyury induction was significantly seen in CHIR 3 uM but not 1 uM (FIG. 7A,C).
  2. 2 d after AA treatment, downregulation of Brachyury expression was delayed in CHIR 1 uM (FIG. 7A) whereas Sox17 expression was significantly lower (7B, D)

The data indicates that PS formation is delayed at Chir concentrations under 1 uM, unabling further progression toward DE when AA is added.

Example 9

DE Induction After CHIR Pre-Treatment in Other Cell Culture Systems

Figure 8:
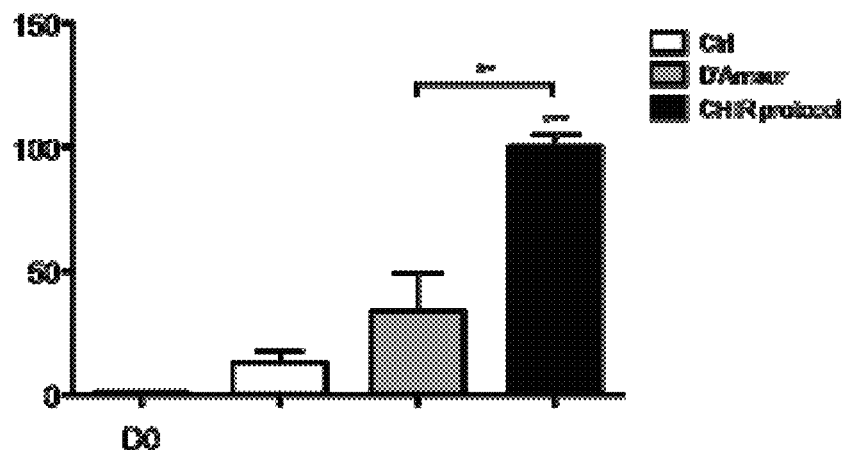
FIG. 8 shows gene expression of SOX17 D3 after CHIR pre-treatment or after the D'Amour protocol in the mTeSR system (FIG. 8).
Figure 9:
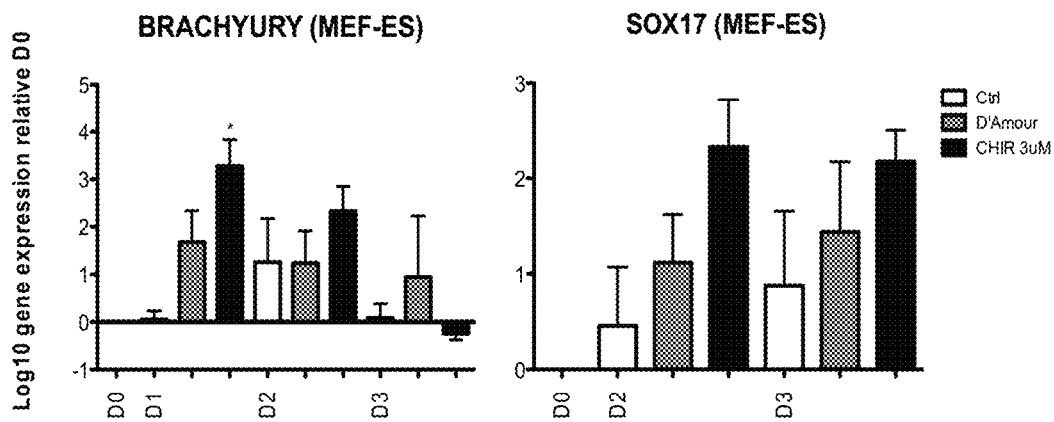
FIG. 9 shows gene expression levels of markers Brachyury and SOX17 at D0, D2 and D3 when cultured on MEF feeders.

The effect on OCT4 downregulation and T/SOX17 upregulation D3 after CHIR pre-treatment was also superior to the D'Amour protocol in other hESC feeder free culture systems such as mTeSR (FIG. 8A Table 4) and in hESCs grown on MEF feeders (FIG. 9).

TABLE 4

Oct4 and Sox17 expression in the mTeSR system
Immunostainings and OCT4/SOX17+ cell quantification

| Exp | Control | | D'Amour | | Chir 7 μM | |
|---|---|---|---|---|---|---|
|  | Oct4 | Sox17 | Oct4 | Sox17 | Oct4 | Sox17 |
| ME16b | 35.51 | 24.6 | 9.86 | 64.77 | 6.97 | 62.62 |
| ME18b | 79.86 | 0.43 | 14.31 | 57.46 | 2.53 | 82.87 |
| ME21a | 64.63 | 13.9 | 31.13 | 56.82 | 0.95 | 91.36 |
| Mean | 60 | 13.0 | 18.4 | 59.7 | 3.5 | 79.0 |

REFERENCES

Amen, J., A. Stahlberg, et al. (2010). "FGF2 specifies hESC-derived definitive endoderm into foregut/midgut cell lineages in a concentration-ᴀ •dependent manner." Stem Cells 28(1): 45-56.

Chung et al. (2008). "Human embryonic stem cells lines generated without embryo destruction". Cell Stem Cell 2.

Geens et al. (2009). "Human embryonic stem cell lines derived from single blastomeres of two 4-cell stage embryos". Human reproduction.

Hanna, J., A. W. Cheng, et al. (2010). "Human embryonic stem cells with biological and epigenetic characteristics similar to those of mouse ESCs." Proc Natl Acad Sci U S A 107(20): 9222-9227.

Jiang, J., M. Au, et al. (2007). "Generation of insulin-producing islet-like clusters from human embryonic stem cells." Stem Cells 25(8): 1940-1953.

Klimanskaya et al. (2006). "Human embryonic stem cell lines derived from single blastomeres". Nature Letters.

Kroon, E., L. A. Martinson, et al. (2008). "Pancreatic endoderm derived from human embryonic stem cells generates glucose-responsive insulin-ᴀ •secreting cells in vivo." Nat Biotechnol 26(4): 443-452.

Mazumdar, J., W. T. O'Brien, et al. (2010). "02 regulates stem cells through Wnt/beta-ᴀ •catenin signalling."Nat Cell Biol 12(10): 1007-1013.

Sato, N., L. Meijer, et al. (2004). "Maintenance of pluripotency in human and mouse embryonic stem cells through activation of Wnt signalling by a pharmacological GSK•3-specific inhibitor." Nat Med 10(1): 55-63.

Wagner, R. T., X Xu, et al. (2010). "Canonical Wnt/beta-ᴀ •Catenin Regulation of Liver Receptor Homolog-1 (Lrh•1) Mediates Pluripotency Gene Expression." Stem Cells.

Yang, J., A. L. van Oosten, et al. (2010). "Stat3 Activation is limiting for reprogramming to ground state pluripotency." Cell Stem Cell 7(3): 319-328.

The invention claimed is:

1. A method for differentiating human embryonic stem cells into definitive endoderm cells, comprising:
  (a) incubating human embryonic stem cells in a first medium comprising CHIR in a range of 2-7 μM, wherein activin A is not present in the medium; and
  (b) subsequently incubating the stem cells in a second medium comprising activin A, wherein CHIR is not present in the second medium; and wherein human definitive endoderm cells are obtained.

2. The method according to claim 1, wherein the concentration of CHIR is at least about 3 μM.

3. The method according to claim 1, wherein the concentration of CHIR is about 4 μM.

4. The method according to claim 1, wherein the incubating step with CHIR is performed for at least 24 hours.

5. The method according to claim 1, wherein the incubating step with CHIR is performed for 24 hours.

6. The method according to claim 1, wherein the incubating step with CHIR is performed for between 24 and 48 hours.

7. The method according to claim 1, wherein the concentration of activin A is selected from the group consisting of about 80 ng/ml and about 100 ng/ml.

8. The method according to claim 1, wherein the concentration of activin A is 100 ng/ml.

9. The method according to claim 1, wherein the incubating step with activin A is performed for 48 to 72 hours.

10. The method according to claim 2, wherein at least 91.5% of the stem cells after step (b) are positive for SOX17.

11. A method for differentiating human embryonic stem cells into definitive endoderm cells, comprising:
  (a) incubating human embryonic stem cells in a first medium comprising about 2-7 μM CHIR for 24 hours, wherein activin A is not present in the first medium; and (b) subsequently incubating the stem cells in a second medium comprising activin A in a concentration of about 100 ng/ml for 48 to 72 hours, wherein CHIR is not present in the second medium, wherein at least 91.5% of the stem cells after step (b) are positive for SOX17; and wherein human definitive endoderm cells are obtained.

12. The method according to claim 11, wherein the concentration of CHIR is 4 µM and the concentration of activin A is 100 ng/ml.

* * * * *